United States Patent [19]

Steer et al.

[11] 4,232,672
[45] Nov. 11, 1980

[54] OSTOMY COUPLING INCLUDING A VENTING VALVE

[75] Inventors: Peter L. Steer; John V. Edwards, both of East Grinstead, England

[73] Assignee: Kingsdown Medical Consultants Limited, London, England

[21] Appl. No.: 930,277

[22] Filed: Aug. 2, 1978

[51] Int. Cl.³ .............................................. A61F 5/44
[52] U.S. Cl. ................................................... 128/283
[58] Field of Search ........................................ 128/283

[56] References Cited

U.S. PATENT DOCUMENTS

| | | | |
|---|---|---|---|
| 1,656,328 | 1/1928 | Cras | 128/283 |
| 2,054,535 | 9/1935 | Diack | 123/283 |
| 2,327,514 | 8/1943 | Fenwick | 128/283 |
| 2,496,175 | 1/1950 | Perry | 128/283 |
| 2,542,233 | 2/1951 | Carrol | 128/283 |
| 2,544,579 | 3/1951 | Ardnwe | 128/283 |
| 2,555,086 | 5/1951 | Guinn | 128/283 |
| 2,652,055 | 9/1953 | Baron | 128/283 |
| 2,655,153 | 10/1953 | Klotz | 128/283 |
| 2,667,167 | 1/1954 | Raiche | 128/283 |
| 2,669,235 | 2/1954 | Burton | 128/283 |
| 2,679,248 | 5/1954 | Fullaway | 128/283 |
| 2,688,327 | 9/1954 | Berg | 128/283 |
| 2,868,204 | 1/1939 | Walker | 128/283 |
| 3,039,464 | 6/1962 | Galindo | 128/283 |
| 3,216,420 | 11/1965 | Smith et al. | 128/283 |
| 3,339,546 | 9/1967 | Chen | 128/156 |
| 3,439,677 | 4/1969 | Bonfils | 128/283 |
| 3,759,260 | 9/1973 | Nolan et al. | 128/283 |
| 3,804,091 | 4/1974 | Nolan et al. | 128/283 |
| 3,865,109 | 2/1975 | Elmore | 128/283 |
| 3,952,727 | 4/1976 | Nolan et al. | 128/283 |

FOREIGN PATENT DOCUMENTS

| | | |
|---|---|---|
| 631987 | 12/1961 | Canada . |
| 2310739 | 10/1936 | France . |
| 217480 | 9/1924 | United Kingdom . |
| 555852 | 9/1943 | United Kingdom . |
| 576181 | 3/1946 | United Kingdom . |
| 648718 | 1/1951 | United Kingdom . |
| 785562 | 10/1957 | United Kingdom . |
| 1212904 | 11/1970 | United Kingdom . |
| 1295252 | 11/1972 | United Kingdom ................... 128/283 |
| 1301101 | 12/1972 | United Kingdom . |
| 1363644 | 8/1974 | United Kingdom . |
| 1416594 | 12/1975 | United Kingdom . |

Primary Examiner—C. Fred Rosenbaum
Attorney, Agent, or Firm—Lawrence S. Levinson; Stephen B. Davis

[57] ABSTRACT

A valve device which permits an ostomate to selectively filter and vent gas from an ostomy appliance. The appliance comprises as a first coupling member a surgical dressing having an adhesive layer and a flange having an upstanding annular wall or projection. The annular wall has one or more openings leading to a filter compartment. The openings are controlled by valves operated by means of a push button at the outer edge of the filter compartment. The adhesive layer and the flange have an aperture so that the dressing can be attached to the body around the stoma. This first coupling member is employed in conjunction with a second coupling member which is an ostomy bag having a channel surrounding the stomal bag opening which sealingly engages the upstanding annular wall of the first coupling member.

6 Claims, 7 Drawing Figures

OSTOMY COUPLING INCLUDING A VENTING VALVE

BACKGROUND OF THE INVENTION

Most ostomates employ some type of bag or pouch system to collect bodily wastes discharged from their surgically created stoma. Today, such bags are generally formed of light weight, odor proof, flexible polymeric materials and the collection systems are designed to be inconspicuous and permit the ostomate to engage in normal physical activity. However, many ostomates, particularly immediately following surgery, have fears concerning their ability to resume a "normal" life. These fears center around worries that the collection system will leak or that odor will escape and that the system will be noticeable even through their outer clothing. Part of these problems are due to the discharge of flatus into the bag which can cause an embarrassing distension of the bag.

In order to overcome the problem of gas build up within the collecting system, it had been suggested to provide a vent opening either in the bag or in the portion of the device which attaches to the body. Devices having simple vent openings are shown in U.S. Pat. Nos. 1,656,328; 2,496,175; 2,542,233; 2,652,055; 2,655,153; 2,679,248; 3,089,493; and 3,055,368; British Patent Nos. 217,480; 555,852; 576,181; and 785,562; and Canadian Patent No. 631,987. Other devices have combined vent openings with filtering or deodorizing means as note U.S. Pat. Nos. 2,327,514; 2,544,579; 2,555,086; 2,669,235; 2,688,327; 3,439,677; 3,759,260; 3,804,091; and 3,952,727; British Patent No. 1,416,594 and French Patent No. 2,310,739. Some devices have also been suggested in which the bag or collecting receptacle includes a venting valve as note U.S. Pat. Nos. 3,039,464 and 3,216,420 and British Patent No. 576,181. Also, a venting valve is disclosed as part of the bag clamping ring in British Patent No. 1,212,904.

RELATED APPLICATION

The valve device of this application is employed with the ostomy appliance disclosed and claimed in our pending application U.S. Ser. No. 881,274 filed on Feb. 27, 1978.

SUMMARY OF THE INVENTION

This invention is directed to a surgical dressing having an adhesive layer which attaches the device to the body and a flange having an upstanding annular wall or projection. The annular wall has one or more openings leading to a filter compartment. The openings are controlled by valves operated by means of a push button at the outer edge of the filter compartment.

The adhesive layer and the flange have a circular aperture for attachment of the dressing around the stoma.

The dressing as described above is employed in conjunction with an ostomy bag having an aperture or channel around the stomal opening. The channel is dimensioned so as to sealingly engage the upstanding annular wall.

BRIEF DESCRIPTION OF THE DRAWINGS

FIGS. 3 to 6 are substantially duplicates of FIGS. 1 to 3 and 6 in U.S. Ser. No. 881,274.

DETAILED DESCRIPTION

Figure 1:
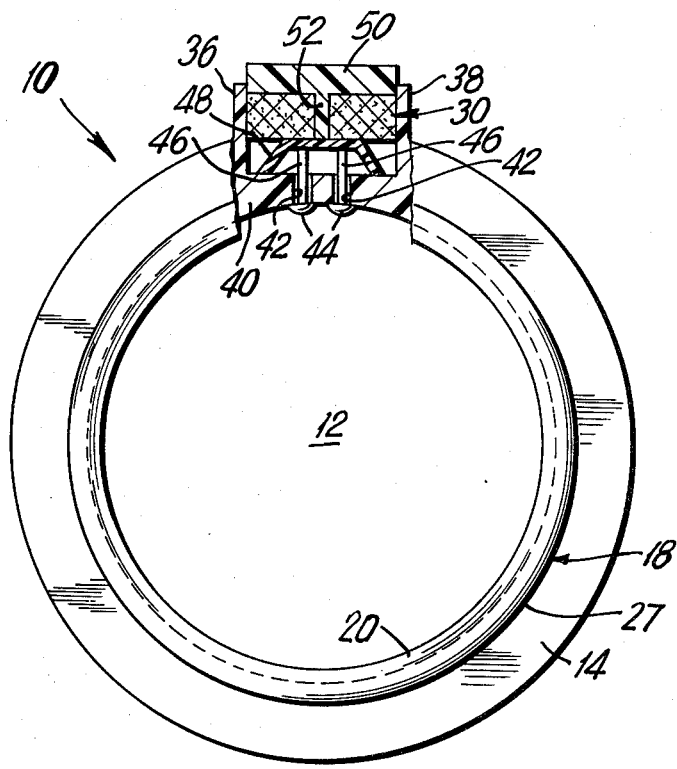
FIG. 1 is a front elevation view of the coupling member of this invention which includes a valve for controlling exit of gases.
Figure 2:
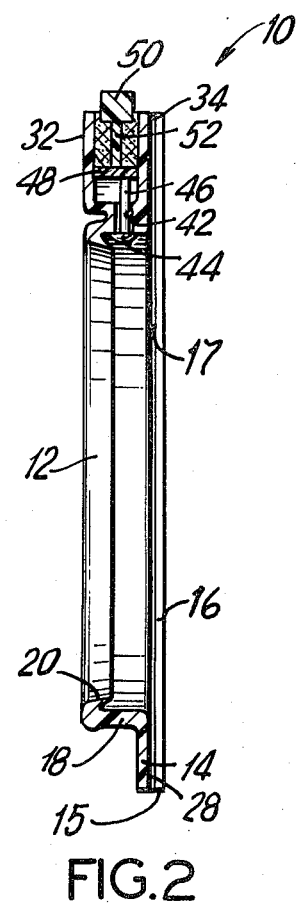
FIG. 2 is a vertical axial section of the coupling member shown in FIG. 1.

Referring firstly to FIGS. 1 and 2, there is illustrated a first coupling 10 which is secured to a pad 15 to form a surgical dressing. The coupling 10 has a central aperture 12, an outwardly extending flange 14, and an upwardly extending annular wall 18. The wall 18 has an integral inwardly-turned flexible sealing strip 20. The pad (shown in FIGS. 2 and 3) is preferably a thin film 17 of polymeric material having an adhesive layer 16 adapted to seal the device to the body. The adhesive material preferably contains one or more water soluble or water swellable hydrocolloids and an elastomeric substance as taught by Chen in U.S. Pat. No. 3,339,546. The polymeric layer of the pad is secured by adhesive or other means to the surface 28 of flange 14. Instead of employing a pad, a layer 16 of adhesive material could be applied directly to surface 28 of flange 14.

A filter compartment 30 is located at the top of coupling 10 when in its position of normal use. The filter compartment 30 is defined by front and rear walls 32 and 34 and lateral walls 36 and 38. Its base 40 is formed by an extension of annular wall 18. The base has one or more holes 42 therethrough, preferably two holes, and these holes can be closed at their lower ends, that is, where they enter the central aperture 12, by respective valves 44. Each valve 44 is carried by a stem 46 and this is connected to a bent strip resilient member which may be of any suitable resilient material such as a synthetic plastics or a springy metal. The resilient member is shown at 48 and it is in turn connected to a push button 50 by a web 52. The push button 50 closes the open top of the compartment 30. The compartment 30 contains any suitable filter material for example activated woven carbon cloth as described in British Patent No. 1,301,101 or activated carbon granules or other suitable gas absorbing material.

Figure 4:
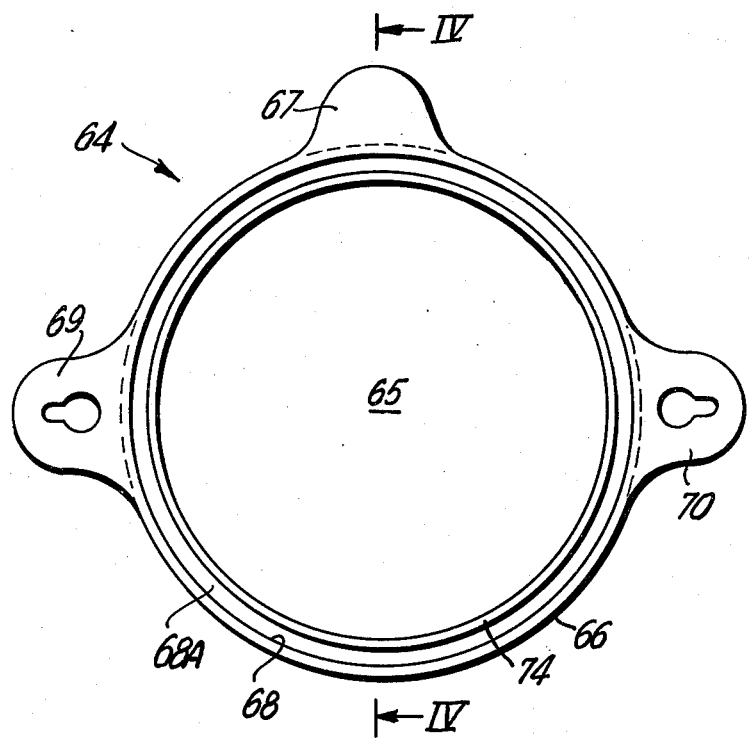
FIG. 4 is an elevation view of the second coupling member affixed to the ostomy bag.
Figure 5:
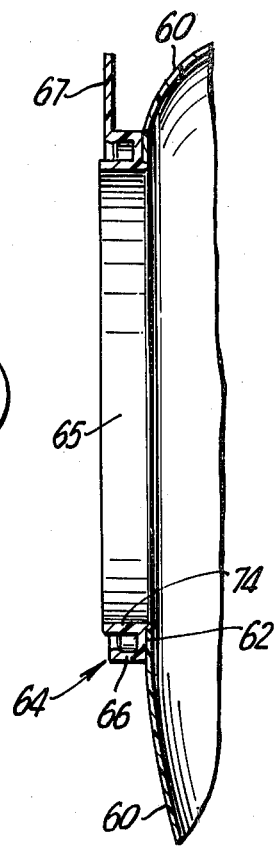
FIG. 5 is a vertical axial section on the line IV—IV through the coupling member shown in FIG. 4.
Figure 6:
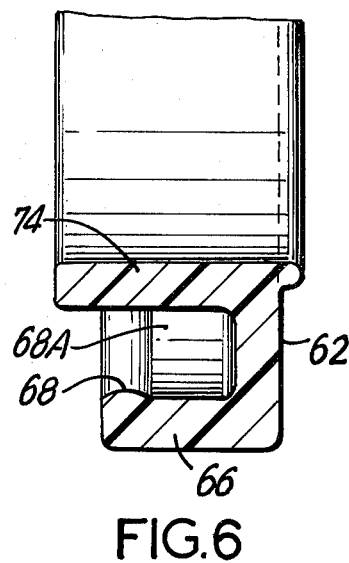
FIG. 6 is an enlarged section taken in a vertical (or any radial) plane showing one form of rim construction of the coupling member shown in FIGS. 4 and 5.
Figure 7:
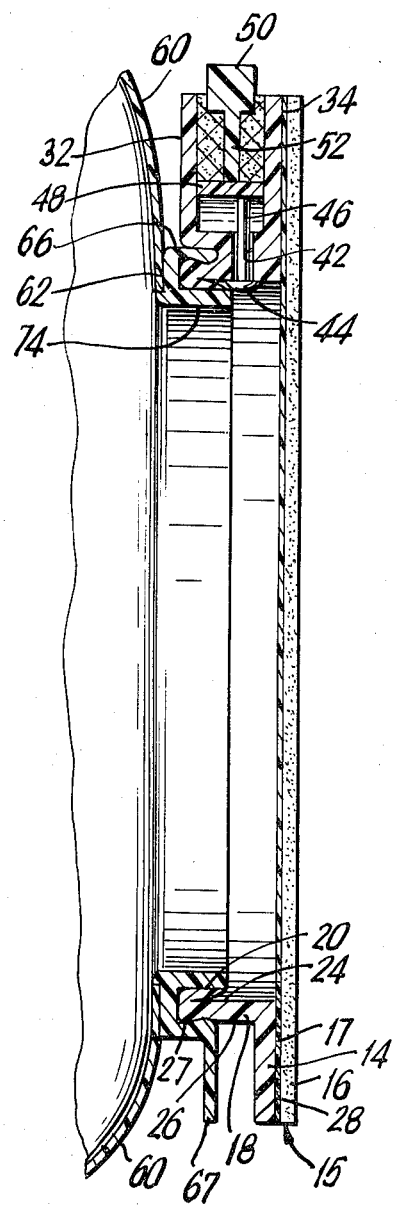
FIG. 7 is a vertical axial section of the coupling members of FIGS. 1 to 3 and FIGS. 4 to 6 when coupled.

The second coupling member 64 is illustrated in FIGS. 4 to 6 and consists of an ostomy bag 60 of plastics material secured by heat welding to a surface 62 of the coupling member 64. The coupling member 64 is circular and defines an aperture 65 which in use surrounds the user's stoma.

The bag 60 can vary. For example, a colostomate would employ a sealed bag whereas an ileostomate would employ a bag having a drainable bottom opening.

Referring to FIG. 6, the second coupling member 64 is of channel-shape seen in any radial cross-section and has a radially inner wall or limb 74 and a radially outer wall or limb 66.

A rim 68 extends inwardly around the inner periphery of the wall 66 and, together with the wall 74, defines a restricted annular mouth or entry 68A into which, in use, the annular wall 18 of the coupling member 10 is pushed to firmly connect the first and second coupling members. Three ears 67, 69, and 70 (FIG. 4) are secured to or molded integrally with the channel and each may serve to be gripped and pulled by the user when he wishes to separate the bag 60 from the pad. The ears 69 and 70 also serve for attachment of a belt if desired. For convenience of the user, the ear 67 may be located at any position around the axis and need not be at "12 o'clock" as illustrated.

Figure 3:
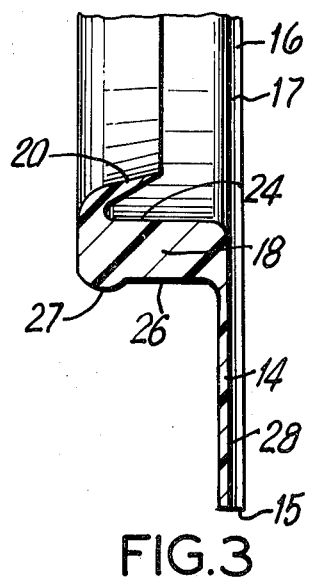
FIG. 3 is an enlargement of part of FIG. 2.

As shown in detail in FIG. 3, the annular wall 18 includes a thin resilient flexible and deflectible seal strip 20. As shown, this is of tapering form seen in cross-section and extends at an angle radially inwardly from an inner surface 24 of the annular wall. In use, when the two coupling members are engaged, it springs radially inwardly to firmly engage the radially-inner wall 74 of the second coupling member to enhance the tight sealing properties of the coupling. Another surface 26 of the annular wall may be provided as shown with a peripheral rim 27 which cooperates with the rim 68 in providing mechanical security.

The operation of the device is simple. When a user of the surgical dressing wishes to vent gases from the bag, he presses downward upon the button 50 which deforms the resilient member 48 and pushes the valve 44 away (generally radially inwardly) from the ends of the holes 42. Gases can then pass from the aperture 12 through the filter compartment 30 and out around the edges of the button 50 which is dimensioned so that it is not a tight fit within the top of the compartment 30.

What is claimed is:

1. An ostomy appliance comprising a pad of polymeric material having an adhesive layer on one side and a radially extending flange permanently bonded to the other side, said adhesive layer and said flange having an aperture permitting the appliance to fit around the stoma, said flange having an upwardly extending annular wall to which an ostomy bag can be readily attached, a filter compartment affixed to a portion of the outer periphery of said annular wall, said annular wall having one or more openings leading into said filter compartment, said openings being controlled by valves which are connected by a resilient member to a push button located at the outer periphery of said filter compartment so that in the normal state said valves seal said openings but by pushing down on said button said valves will permit gas to pass through said openings into said filter compartment and finally exit from said filter compartment.

2. The appliance of claim 1 wherein said adhesive contains an elastomer and one or more water soluble or water swellable hydrocolloids.

3. The appliance of claim 2 wherein said annular wall has a thin resilient seal strip extending radially inward from said annular wall.

4. The appliance of claim 3 wherein said filter compartment contains activated carbon.

5. The appliance of claim 4 wherein said filter compartment contains at least one layer of woven activated carbon cloth.

6. The appliance of claim 5 wherein said annular wall has two openings leading to said filter compartment.

* * * * *